(12) United States Patent
Gehringer et al.

(10) Patent No.: US 7,700,732 B2
(45) Date of Patent: Apr. 20, 2010

(54) PREKALLIKREIN DEPLETED PLASMA DERIVED ALBUMIN FRACTION

(75) Inventors: Werner Gehringer, Vienna (AT); Katharina Pock, Streifing (AT)

(73) Assignee: Octapharma AG, Lachen (CH)

( * ) Notice: Subject to any disclaimer, the term of this patent is extended or adjusted under 35 U.S.C. 154(b) by 430 days.

(21) Appl. No.: 10/533,160

(22) PCT Filed: Nov. 25, 2003

(86) PCT No.: PCT/EP03/13239
§ 371 (c)(1),
(2), (4) Date: Oct. 12, 2005

(87) PCT Pub. No.: WO2004/047859
PCT Pub. Date: Jun. 10, 2004

(65) Prior Publication Data
US 2006/0100419 A1    May 11, 2006

(30) Foreign Application Priority Data
Nov. 25, 2002   (EP)   .................................. 02026165

(51) Int. Cl.
C07K 14/00      (2006.01)
(52) U.S. Cl. ...................................... 530/369; 530/362
(58) Field of Classification Search .................. 530/380
See application file for complete search history.

(56) References Cited

U.S. PATENT DOCUMENTS

| | | | |
|---|---|---|---|
| 4,251,510 A | 2/1981 | Tankersley |
| 4,378,346 A | 3/1983 | Tankersley |
| 4,391,801 A | 7/1983 | Ng et al. |
| 4,440,679 A | 4/1984 | Fernandes et al. |
| 4,608,254 A | 8/1986 | Philapitsch et al. |
| 5,094,949 A | 3/1992 | Linnau |
| 5,919,907 A | 7/1999 | Shanbrom |
| 6,693,173 B2 | 2/2004 | Mamidi et al. |

OTHER PUBLICATIONS

Tanaka et al., "Purification of human albumin by the combination of the method of Cohn with liquid chromatography," Brazilian Journal and Biological Research, 1998, 31, pp. 1383-1388.*
Tanaka et al., "High quality human immunoglobulin G purified from Cohn fractions by liquid chromatography," Brazilian Journal and Biological Research, 2000, 33, pp. 27-30.*
Matejtschuk et al., "Production of human albumin solution: a continually developing colloid," British Journal of Anesthesia 2000, 85, vol. 6, pp. 887-95.*
"Production of human albumin solution: a continually developing colloid," P. Matejtschuk et al., British Journal of Anaesthesia 85(6): 887-95 (2000).
"All about Albumin," Theodore Peters, Jr., Academic Press, p. 295 (1966).
"Temperature Sensitivity within the Pasteurization Temperature Range of Prekallikrein Activator in Stable Plasma Protein Solution (SPPS)," P.B. Marley et al., J.B. Lippincott Co., vol. 21, No. 3, pp. 320-324 (1981).
"Viral Validation of the Manufacturing Process of High Purity Albumin From Placentas," M. Grandgeorge et al., Dev. Biol., vol. 81, pp. 237-244 (1993).
"A New High Quality Albumin for Therapeutic Use," Jørgen F. Hansen et al., Develop. biol. Standard, 48, pp. 105-112 (1981).
Tanaka, K., et al., "Purification of human albumin by the combination of the method of Cohn with liquid chromatography," Brazilian J. Med. Biol. Res. 31:1383-1388, Associação Brasileira de Divulgação Cientifica (1998).
Véron, J.-L., et al., "Combined Cohn/chromatography purification process for the manufacturing of high purity human albumin for plasma," Biotechnol. Blood Proteins 227:183-188, Colloque INSERM/John Libbey Eurotext Ltd. (1993).
International Search Report for International Application No. PCT/EP03/13239, European Patent Office, Netherlands, mailed on Jun. 18, 2004.
Che, Y. et al., "Impact of Manufacturing Improvements on Clinical Safety of Albumin; Australian Pharmacovigilance Data for 1988-2005", Critical Care and Resuscitation, vol. 8, No. 4, Dec. 2006.
Kerry, P.J., et al. "Standardization of Prekallikrein Activator (PKA): The 1st International Standard for PKA", National Institute for Biological Standards andControl, London, Oct. 22, 1984.
"Albumin Soultion, Human", European Pharmacopoeia, 1997.
"Human Albumin 20% lmmuno. Human Albumin 25% Immuno", Immuno AG, Aug. 1990.

* cited by examiner

Primary Examiner—Karen Cochrane Carlson
(74) Attorney, Agent, or Firm—Venable LLP; Ann S. Hobbs

(57) ABSTRACT

An albumin containing fraction having a reduced prekallikrein activator (PKA) content and a method of manufacturing same comprising the steps of:
(a) reconstitution of paste V (Cohn fractionation),
(b) performing a concentration step of the fraction obtained in step (a),
(c) heating the fraction obtained in step (b) in a range of from 50° C. to 70° C. for a sufficient time to pasteurize the fraction, and
(d) optionally filling of the obtained fraction for use.

3 Claims, No Drawings

PREKALLIKREIN DEPLETED PLASMA DERIVED ALBUMIN FRACTION

The present invention pertains to a method of manufacturing an albumin enriched fraction having a reduced prekallikrein activator (PKA) and an albumin containing fraction having a reduced prekallikrein activator (PKA) obtainable according to the method of the invention.

Albumin containing preparations are used as infusion solutions for patients who are in need thereof. In order to have a more physiological environment liquid substitution is infused into patients containing not only salts in physiological concentration but also albumin as extender. Albumin preparations may contain prekallikrein activator, which may lead to unwanted side effects, which may be due to interference of the prekallikrein activator in the renin-angiotensin system.

The object of the present invention was to reduce the PKA content in plasma is derived fractions containing albumin. It was another object to provide an albumin containing fraction having a reduced PKA value.

The object was solved by a method of manufacturing an albumin enriched fraction having a reduced prekallikrein activator (PKA) comprising the steps of:

(a) reconstitution of paste V, (Cohn fractionation)

(b) performing a concentration step of the fraction obtained in step (a), (c) heating the fraction obtained in step (b) in a range of from 50° C. to 70° C. for a sufficient time to pasteurize the fraction, and (d) optionally filling of the obtained fraction for use.

In an embodiment of the present invention a second pasteurisation step is performed after filling.

In particular, the incubation step is performed at 50 to 70° C. for duration of at least 5 hours, in particular 10 hours.

Starting with reconstitution of paste V and optionally addition of filter aids a filtration is performed preferably with a filter having a pore size of about 0.2 µm. If necessary, a pH adjustment has to be performed. The pH should be in the range of 7.2-7.6. Typically an ultrafiltration to 8% (w/v) protein content is performed followed by diafiltration and another ultrafiltration for concentration of the protein. This leads to protein concentrations of at least 20%. Then another filtration may be performed preferably with a membrane having a pore size of about 0.2 µm.

Stabilizers are added for example 0.08 mmol/g albumin each of N-acetyl-DL-tryptophan and sodium caprylate, which is followed by a further pH adjustment in a range of 6.7 to 7.3. Adjustment of protein and sodium content is achieved and a bulk pasteurization is performed preferably in a range of 58° C. to 65° C. for at least 9 hours. This step is followed by a sterile filtration. The sample is stored less than 2 weeks at 2° C. to 25° C. The albumin sterile bulk is subjected to a further terminal sterile filtration and filled. After the filling a second pasteurization step under similar conditions as described before can be performed. A further incubation step may be added. After visual inspection the preparation is ready for storage and administration.

The method of the invention also provides an albumin containing fraction having a reduced prekallikrein activator (PKA).

The PKA content of the albumin of the invention is less than 12 IU/ml, preferably 10 IU/ml, wherein the PKA is determined according to European Pharmacopoeia, Fourth Edition, 2.6.15, p. 147-148.

The invention is further described by the following non-limiting examples.

EXAMPLES

Example 1

The paste V is suspended in the 1.6 fold of its weight of water for injections for >6 hours at −2±2° C. Filter aids are added to the product and the preparation is stirred for 30 min. The depth filter is prewashed with water for injections and subsequently with 10% (v/v) ethanol. The solution is clarified by passing through the depth filter and a subsequent 0.2 µm membrane filter. The filter is post-washed with 10% ethanol in water for injections. The pH is adjusted to 7.4±0.2 with 3 M sodium hydroxide solution.

A protein concentration of 8% is obtained by ultrafiltration through membranes with an exclusion limit of 10 kDalton. The concentrate is diafiltered against a ≧3 fold quantity of 0.5 M sodium chloride solution, followed by a ≦3 fold quantity of water for injections. After the diafiltration, the albumin solution is concentrated to a protein concentration of approximately 22% by ultrafiltration at ≦+15° C. The solution is clarified by passing through the depth filter and a subsequent 0.2 µm membrane filter. The depth filter is prewashed with water for injections Subsequently 0.0106 g caprylic acid/g protein and 0.0182 g N-acetyl-DL-tryptophan/g protein are dissolved in 10% (w/v) sodium hydroxide and added to the albumin solution under slow stirring. The pH is adjusted to 7.0±0.3. The albumin solution is adjusted to a protein concentration of 200±10 g/l by adding is water for injections. The sodium content is adjusted to 150±7.5 mmol/l by adding sodium chloride. The solution is agitated for at least 9 hours at 58-65° C. The albumin solution is sterile filtered through a sterilising grade filter membrane of a nominal pore size of typically 0.2 µm. The sterile filter is tested for integrity before and after use by an appropriate test method as recommended by the specification of the manufacturer. The sterile filtered albumin is stored at +2° C.-+25° C. not longer than 2 weeks. The sterile solution is filled using a terminal 0.2 µm sterile filter under aseptic conditions into depyrogenated infusion vials, which are closed with sterilised butyl-stoppers and sealed with aluminium caps. The sterile filter is tested for integrity before and after use by an appropriate test method as recommended by the specification of the manufacturer. The filling volume is monitored throughout the filling process. Pasteurisation is done according European Pharmacopoeia. The final Containers are incubated according European Pharmacopoeia. Following the incubation period, all vials are visually inspected for particulate contamination, turbidity, defects of vials and closures. Defective preparations are rejected. All vials are stored at +2° C. to +25° C.

Example 2

The paste V is suspended in the 1.6 fold of its weight of water for injections for >6 hours at −2±2° C. Filter aids are added to the product and the preparation is stirred for 30 min. The depth filter is prewashed with water for injections and subsequently with 10% ethanol. The solution is clarified by passing through the depth filter and a subsequent 0.2 µm membrane filter. The filter is post-washed with 10% ethanol in water for injections. The pH is adjusted to 7.4±0.2 with 3 M sodium hydroxide solution. A protein concentration of 8% is obtained by ultrafiltration through membranes with an exclusion limit of 10 kDalton. The concentrate is diafiltered against a ≧3 fold quantity of 0.5 M sodium chloride solution, followed by ≦3 fold quantity of water for injections. After the diafiltration, the albumin solution is concentrated to a protein concentration of approximately 26% by ultrafiltration at <+15° C. The solution is clarified by passing through the depth filter and a subsequent 0.2 µm membrane filter. The depth filter is is prewashed with water for injections. Subsequently 0.0106 g caprylic acid/g protein and 0.0182 g N-acetyl-DL-tryptophan/g protein are dissolved in 10% sodium hydroxide and added to the albumin solution under slow stirring. The pH is adjusted to 7.0±0.3. The albumin solution is adjusted to a protein concentration of 250±12 g/l by adding water for injections. The sodium content is adjusted to 150±7.5 mmol/l by adding sodium chloride. The solution is agitated for at least 9 hours at 58-65° C. The albumin solution is sterile filtered through a sterilising grade filter membrane of a nominal pore size of typically 0.2 µm. The sterile filter is tested for integrity before and after use by an appropriate test method as recommended by the specification of the manufacturer. The sterile filtered albumin is stored at +2° C.-+25° C. not longer than 2 weeks. The sterile solution is filled using a terminal 0.2 µm sterile filter under aseptic conditions into depyrogenated infusion vials, which are closed with sterilised butyl-stoppers and sealed with aluminium caps. The sterile filter is tested for integrity before and after use by an appropriate test method as recommended by the specification of the manufacturer. The filling volume is monitored throughout the filling process. Pasteurisation is done according European Pharmacopoeia. The final Containers are incubated according European Pharmacopoeia. Following the incubation period, all vials are visually inspected for particulate contamination, turbidity, defects of vials and closures. Defective preparations are rejected. All vials are stored at +2° C. to +25° C.

Example 3

The paste V is suspended in the 1.6 fold of its weight of water for injections for 6 hours at -2±2° C. Filter aids are added to the product and the preparation is stirred for 30 min. The depth filter is prewashed with water for injections and subsequently with 10% ethanol. The solution is clarified by passing through the depth filter and a subsequent 0.2 µm membrane filter. The filter is post-washed with 10% ethanol in water for injections. The pH is adjusted to 7.4±0.2 with 3 M sodium hydroxide solution. A protein concentration of 8% is obtained by ultrafiltration through membranes with an exclusion limit of 10 kDalton. The concentrate is diafiltered against a >3 fold quantity of 0.5 M sodium chloride solution, followed by a <3 fold quantity of water for injections. After the is diafiltration, the albumin solution is concentrated to a protein concentration of approximately 22% by ultrafiltration less than +15° C. The solution is clarified by passing through the depth filter and a subsequent 0.2 µm membrane filter. The depth filter is prewashed with water for injections. Subsequently 0.0106 g caprylic add/g protein and 0.0182 g N-acetyl-DL-tryptophan/g protein are dissolved in 10% sodium hydroxide and added to the albumin solution under slow stirring. The pH is adjusted to 7.0±0.3. The albumin solution is adjusted to a protein concentration of 200±10 g/l by adding water for injections. The sodium content is adjusted to 150±7.5 mmol/l by adding sodium chloride. The solution is agitated for at least 10 hours at 58-65° C. The albumin solution is sterile filtered through a sterilising grade filter membrane of a nominal pore size of typically 0.2 µm. The sterile filter is tested for integrity before and after use by an appropriate test method as recommended by the specification of the manufacturer. The sterile filtered albumin is stored at +2° C. to +25° C. not longer than 2 weeks. The albumin solution is adjusted to a protein concentration of 50±2.5 g/l by adding water for injections. The pH is adjusted to 7.0±0.3. The sodium content is adjusted to 150±7.5 mmol/l by adding of sodium chloride. The albumin solution is stored at +2° C. to +25° C. not longer than 24 hours until filling. The sterile solution is filled using a terminal 0.2 µM sterile filter under aseptic conditions into depyrogenated infusion vials, which are closed with sterilised butyl-stoppers and sealed with aluminium caps. The sterile filter is tested for integrity before and after use by an appropriate test method as recommended by the specification of the manufacturer. The filling volume is monitored throughout the filling process. Pasteurization is done according European Pharmacopoeia. The final containers are incubated according to European Pharmacopoeia. Following the incubation period, all vials are visually inspected for particulate contamination, turbidity, defects of vials and closures. Defective preparations are rejected. All vials are stored at +2° C. to +25° C.

Prekallikrein Activator

Prekallikrein activator (PKA) activates prekallikrein to kallikrein and may be assayed by its ability to cleave a chromophore from a synthetic peptide is substrate so that the rate of cleavage can be measured spectrophotometrically and the concentration of PKA calculated by comparison with a reference preparation calibrated in International Units.

The International Unit is the activity of a stated amount of the International Standard which consists of freeze-dried prekallikrein activator. The equivalence in International Units of the International Standard is stated by the World Health Organization.

Preparation of Prekallikrein Substrate

To avoid coagulation activation, blood or plasma used for the preparation of prekallikrein must come into contact only with plastics or silicone-treated glass surfaces. Draw 9 volumes of human blood into 1 volume of anticoagulant solution (ACD, CPD or 38 g/l sodium citrate) to which 1 mg/ml of hexadimethrine bromide has been added. Centrifuge the mixture at 3600 g for 5 min. Separate the plasma and centrifuge again at 6000 g for 20 min to sediment platelets. Separate the platelet-poor plasma and dialyse against 10 volumes of buffer A for 20 h. Apply the dialysed plasma to a chromatography column containing agarose-DEAE for ion exchange chromatography which has been equilibrated in buffer A and is equal to twice the volume of the plasma. Elute from the column with buffer A at 20 ml/cm²/h. Collect the eluate in fractions and record the absorbance at 280 nm (2.2.25). Pool the fractions containing the first protein peak so that the volume of the pool is about 1.2 times the volume of the platelet-poor plasma.

Test the substrate pool for absence of kallikrein activity by mixing 1 part with parts of the pre-warmed chromogenic substrate solution to be used in the assay and incubate at 37° C. for 2 min. The substrate is suitable if the increase in absorbance is less than 0.001 per minute. Add to the pooled solution 7 g/l of sodium chloride and filter using a membrane filter (porosity 0.45 µm). Freeze the filtrate in portions and store at -25° C.; the substrate may be freeze-dried before storage.

Carry out all procedures from the beginning of the chromatography to freezing in portions during a single working day.

Assay

The assay is preferably carried out using an automated enzyme analyser at 37° C., with volumes, concentration of substrates and incubation times adjusted so that the reaction rate is linear at least up to 35 IU/ml. Standards, samples and prekallikrein substrate may be diluted as necessary using buffer B.

Incubate diluted standards or samples with prekallikrein substrate for 10 min such that the volume of the undiluted sample does not exceed 1/10 of the total volume of the incubation mixture to avoid errors caused by variation in ionic strength and pH in the incubation mixture. Incubate the mixture or a part thereof with at least an equal volume of a solution of a suitable synthetic chromogenic substrate, known to be specific for kallikrein (for example, N-benzoyl-L-prolyl-L-phenylalanyl-L-arginine 4-nitroanilide acetate R or D-prolyl-L-phenylalanyl-L-arginine-4-nitroanilide-dihydrochloride R), dissolved in buffer B. Record the rate of change in absorbance per minute for 2 min to 10 min at the wavelength specific for the substrate used. Prepare a blank for each mixture of sample or standard using buffer B instead of prekallikrein substrate.

Correct ΔA/min by subtracting the value obtained for the corresponding blank. Plot a calibration curve using the values thus obtained for the reference preparation and the respective concentrations; use the curve to determine the PKA activity of the preparation to be examined.

Buffer A

| | |
|---|---|
| Tris(hydroxymethly)aminomethane | 6.055 g |
| Sodium chloride | 1.17 g |
| Hexadimethrine bromide | 50 mg |
| Sodium azide | 0.100 g |

Dissolve the ingredients in water, adjust to pH 8.0 with 2 M hydrochloric acid and dilute to 1000 ml with water.

| | |
|---|---|
| Tris(hydroxymethyl)aminomethane | 6.055 g |
| Sodium chloride | 8.77 g |

Dissolve the ingredients in water adjust to pH 8.0 with 2 M hydrochloric acid and dilute to 1000 ml with water.

| Production step | PKA value (according to the invention) | PKA value (comparative example) |
|---|---|---|
| After IPBP* and sterile filtration | 3 IU/ml | n.a.** |
| After pasteurisation in final container | <2 IU/ml | 5 IU/ml |
| After incubation | 4 IU/ml | 18 IU/ml |
| After IPBP* and sterile filtration | <2 IU/ml | n.a.** |
| After pasteurisation in final container | <2 IU/ml | 2 IU/ml |
| After incubation | 3 IU/ml | 12 IU/ml |
| After IPBP* and sterile filtration | <2 IU/ml | n.a.** |
| After pasteurisation in final container | <2 IU/ml | 5 IU/ml |
| After incubation | 2 IU/ml | 20 IU/ml |

*IBPP in process bulk pasteurisation
**n.a. not applicable

The invention claimed is:

1. A method of manufacturing an albumin enriched fraction having a reduced prekallikrein activator (PKA) content consisting of:
   (a) reconstitution of paste V (Cohn fractionation) to form a first fraction;
   (b) concentrating the first fraction obtained in step (a) to obtain a concentrated fraction;
   (c) addition of stabilizers to the concentrated fraction to obtain a stabilized fraction;
   (d) pasteurizing the stabilized fraction obtained in step (c) for a time period of at least nine hours at a temperature of 58° C. to 65° C. to obtain a pasteurized fraction;
   (e) filling vials with the pasteurized fraction;
   (f) performing a second pasteurization with the filled vials of step (e); and
   (g) incubating the vials to obtain an albumin enriched fraction having a PKA content of less than 12 IU/ml.

2. The method of claim 1 wherein the second pasteurization step is performed for a time period of at least nine hours at a temperature of 58° C. to 65° C.

3. The method of claim 1, wherein pasteurization is performed for a time period of at least 10 hours.

* * * * *